United States Patent [19]
Terajima et al.

[11] Patent Number: 4,663,080
[45] Date of Patent: May 5, 1987

[54] HYPO-ALLERGENIC MOSS OIL AND PRODUCTION PROCESS THEREOF

[75] Inventors: Yushi Terajima; Katsuhiko Tokuda; Shoji Nakamura; Keiichi Uehara; Hideyuki Ichikawa; Shinobu Iwakami, all of Yokohama, Japan

[73] Assignee: Shiseido Company Ltd., Tokyo, Japan

[21] Appl. No.: 864,934

[22] Filed: May 20, 1986

[30] Foreign Application Priority Data

| | | | |
|---|---|---|---|
| May 21, 1985 | [JP] | Japan | 60-106827 |
| May 21, 1985 | [JP] | Japan | 60-106829 |
| Jul. 12, 1985 | [JP] | Japan | 60-153657 |
| Jul. 12, 1985 | [JP] | Japan | 60-153658 |

[51] Int. Cl.[4] .......... A61K 7/46; C11B 9/00
[52] U.S. Cl. .......... 252/522 R
[58] Field of Search .......... 252/522 R, 522 A

[56] References Cited

U.S. PATENT DOCUMENTS

| | | | |
|---|---|---|---|
| 2,976,321 | 3/1961 | Dorsky et al. | 252/522 R |
| 3,150,050 | 9/1964 | Safrin et al. | 252/522 R |
| 3,681,470 | 8/1972 | Kitchen et al. | 252/522 R |
| 3,839,233 | 10/1974 | Wight et al. | 252/522 R |
| 4,308,179 | 12/1981 | Celli | 252/522 R |
| 4,464,290 | 8/1984 | Ohta et al. | 252/522 R |
| 4,613,513 | 9/1986 | Hussein | 426/651 |

OTHER PUBLICATIONS

Poucher et al. "Perfumes, Cosmetics and Soaps" (1959), pp. 306-307.

*Primary Examiner*—Werren B. Lone
*Attorney, Agent, or Firm*—Sprung Horn Kramer & Woods

[57] ABSTRACT

Hypo-allergenic moss oil from which ethyl hematommate and/or ethyl chlorohematommate or atranorin and/or chloroatranorin are substantially removed. This hypo-allergenic moss oil can be produced by chromatography separation, solvent extraction, countercurrent partition, and/or membrane separation or catalytic hydrogenation treatment and/or alkaline treatment.

6 Claims, 11 Drawing Figures

(1) MASS SPECTRUM OF ETHYL HEMATOMMATE (2) MASS SPECTRUM OF ETHYL CHLOROHEMATOMMATE

HYPO-ALLERGENIC MOSS OIL AND PRODUCTION PROCESS THEREOF

BACKGROUND OF THE INVENTION

1. Field of the Invention

The present invention relates to a hypo-allergenic moss oil and a process for producing the same. The moss oil used herein means an extracted oil obtained by the extraction from epiphytic moss on the bark of trees and generally includes, for example, oakmoss oil, treemoss oil, cedarmoss oil, and moss oils produced in China.

2. Description of the Related Art

Oakmoss, Mousse de chêne (Evernia Prunastri L. Ach.) was used for baking bread in ancient Egypt and also widely used as a universal panacea in the East during the 12th century.

Oakmoss is now recognized as an important perfume starting material and that oil is extremely widely used for the compound perfume of odor products, cosmetics, soaps, and detergents, similarly, Treemoss, Mousse d'arbre (Evernia furfuracea L. Mann) and cedarmoss are widely used as starting materials similar to oakmoss. Recently, moss produced in China, Evernia mesormopha, and Cetrariastrum nepalensis are being used in the same application fields.

Moss oil is indispensable for constituting the so-called chypre type fragrances and is also frequently used for a base note providing the volume and richness. It is reported in Monographs on Fragrance Raw Materials; Edited by D. L. Opdyke, Pergamon Press (1979) that moss oil is used in the United States in an amount of about 50 tons/year (i.e., oakmoss oil: 34 tons/year, treemoss oil: 16 tons/year).

However, it is reported in, for example, I. Dahlquist, S. Fregert: Contact allergy to atranorin in lichens and perfumes, Contact Dermatitis, 6,111 (1980); P. Thune, Y. Solberg et al: Perfume allergy due to oakmoss and other lichens, Contact Dermatitis, 8,396 (1982); and M. Sandberg, P. Thune: The sensitizing capacity of atranorin, Contact Dermatitis, 11,168 (1984) that moss oils cause positive reactions in patients with cosmetic contact dermatitis. The present inventors conducted allergenicity tests with respect to commercially available moss oils and confirmed, as shown in Comparative Example 1 hereinbelow, that the commercially available moss oils have a very very strong allergenicity.

SUMMARY OF THE INVENTION

Accordingly, an object of the present invention is to eliminate the above-mentioned problems in natural moss oils and to provide hypo-allergenic moss oils.

Another object of the present invention is to provide a process for producing a hypo-allergenic moss oil.

Other objects and advantages of the present invention will be apparent from the following description.

In accordance with the present invention, there is provided a hypo-allergenic moss oil from which either one or both of ethyl hematommate and ethyl chlorohematommate are substantially removed or a hypo-allergenic moss oil from which either one or both of atranorin and chloroatranorin are substantially removed.

This moss oil contains no substantial amount of (A) substances having a count number of 40.5 to 45 or (B) substances having a count number of 30 to 45, determined by gel permeation chromatography (i.e., GPC) in four TSKGEL G2000H8 columns (HLC-802UR manufactured by Toyo Soda Kogyo Co. in Japan) under the conditions defined below.

Column temperature: 40° C.,
Solvent: Tetrahydrofuran (i.e., THF),
Flow rate: 1.2 ml/min at 90 kg/cm2,
Sample concentration: 0.2 to 2% by weight in THF,
Sample amount: 100 μl, and
Detector: Differential refractive index (i.e., RI) detector.

In accordance with the present invention, there is also provided a process for producing a hypo-allergenic moss oil in which (i) the hypo-allergenic moss oil is separated from a starting moss oil with at least one treatment selected from the group consisting of chromatography including column chromatography, preparative GPC, and high performance liquid chromatography (i.e., HPLC), solvent extraction, countercurrent partition and membrane separation and/or (ii) the hypo-allergenic moss oil is subjected to either one or both of the catalytic hydrogenation and alkaline treatments.

BRIEF DESCRIPTION OF THE DRAWINGS

The present invention will be better understood from the description set forth below with reference to the accompanying drawings in which.

DESCRIPTION OF THE PREFERRED EMBODIMENTS

Figure 1:
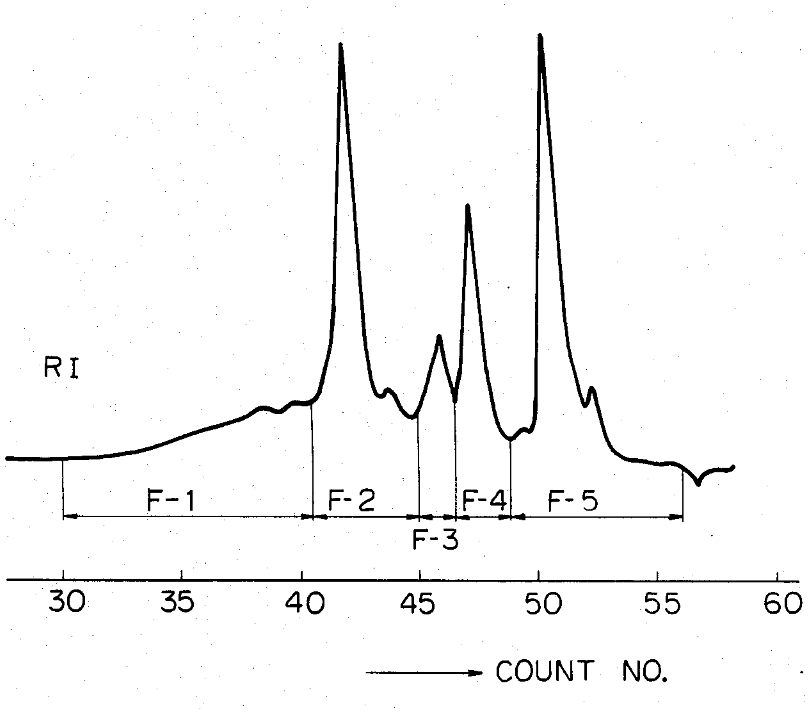
FIG. 1 is a GPC chromatogram and a GPC separation fraction of commercially available oakmoss oil #1.

According to a study by the present inventors, it has been found that the allergenic substances are concentrated in certain fractions of the natural moss oil as shown in Comparative Example 2 mentioned hereinbelow. After an extensive study of the allergenic fractions, we have found that the allergenic substances contained in the specific allergenic fractions include the following four compounds.

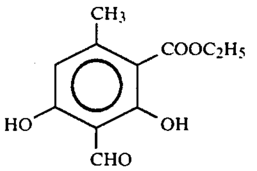

Ethyl hematommate

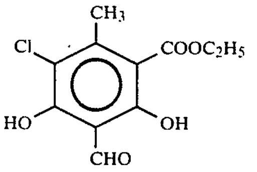

Ethyl chlorohematommate

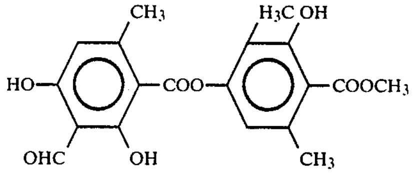

Atranorin

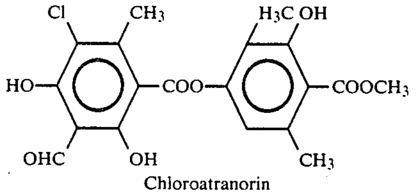

Chloroatranorin

According to our study, moss oils not containing the ethyl hematommate and ethyl chlorohematommate (i.e., hematommates) and the atranorin and chloro atranorin (i.e., atranorins) as well as (A) substances having a count number of 40.5 to 45 (i.e., substances A) or (B) substances having a count number of 30 to 45 (i.e., substances B), determined by the above-mentioned gel permeation chromatography have no substantial allergenicity. Such moss oils can be produced from the natural moss oils by various separation techniques for removing the allergenic substances or by subjecting the moss oils to a catalytic hydrogenation and/or alkaline decomposition treatment (i.e., alkaline treatment) or by any combination of these techniques. Thus, the desired hypo-allergenic moss oils can be advantageously obtained while retaining the inherent odor of the moss oils.

The typical treatment and separation methods will now be explained below.

(1) Catalytic hydrogenation treatment

The catalytic hydrogenation methods typically include normal pressure methods and high pressure methods. It has been found that the hydrogenation of the hematommates can be quantitatively carried out even under a normal pressure, when a suitable catalyst is selected. When a large amount of moss oil is hydrogenated, a high pressure method is advantageously used. However, the reaction temperature is preferably not higher than 100° C. for the reason that the possible thermal decomposition of the components providing the desired odor should be avoided.

Examples of the catalysts usable for the catalytic hydrogenation of the moss oil are any conventional hydrogenation catalysts such as Ni catalysts and platinum metal (i.e., Pt, Pd, Ph, and Ru) catalysts. Of these conventional hydrogenation catalysts, the use of 10% palladium supported on activated carbon (i.e., 10% Pd/c) or a Raney Ni catalyst is preferable for the purpose of the present invention. The preferable amount of the catalyst is 5% to 30%, by weight of the moss oil to be hydrogenated. The hydrogenation reaction is usually carried out in, for example, an organic solvent such as methanol and ethanol at room temperature for 5 to 24 hours. Thus, the quantitative hydrogenation is effected.

(2) Alkaline Treatment

The moss oil is subjected to alcoholic decomposition or hydrolysis in an aqueous alcoholic alkaline solution. Examples of the alkaline compounds usable in the alkaline treatment are sodium hydroxide (NaOH), potassium hydroxide (KOH), and sodium carbonate, and examples of the alcohols are methanol and ethanol.

According to the alkaline treatment, hematommates and atranolins are readily decomposed, whereby the allergenicity of these compounds is reduced or eliminated. Although there are no critical limitations to the alkaline treatment conditions, the alkaline treatment is preferably carried out at a temperature of room temperature to 50° C. at an alkaline solution concentration of $10^{-4}$ to 1N.

(3) Preparative Column Chromatography

According to this method, the desired hypo-allergenic moss oil can be effectively produced by treating the starting moss oil with an non-polar or less-polar solvent such as pentane, hexane, benzene, or ether by using a column packed with an adsorbent. Examples of such adsorbents are activated carbon, activated clay, silica gel, synthetic adsorbents such as Amberlyte XAD series (Trademark, manufactured by Rhom & Haas Co., Ltd.), ion exchange resins such as Amberlyst series (Trademark, manufactured by Rhom & Haas Co., Ltd.). The preferable adsorbents are silica gels (e.g., Kieselgel 60 manufactured by Merck & Co.).

On the other hand, the moss oil can be effectively separated with a polar solvent such as water, methanol, ethanol, and chloroform, by using a column packed with dextran gel having a three-dimensional structure such as Sephadex, Sephadex-LH (Trademark, series manufactured by Pharmacia Fine Chemicals Co., Ltd.).

(4) Preparative GPC

According to this method, the hypo-allergenic moss oil can be effectively produced by using, typically, a GPC column for organic solvents. The preferable exclusion limit of the GPC column is $5\times10^3$ to $1\times10^4$ and the typical solvents usable in the preparatory GPC are tetrahydrofuran (THF) and chloroform. The separation is carried out in accordance with the chromatogram pattern obtained by an RI detector.

(5) Preparative HPLC

According to this method, the desired hypo-allergenic moss oil can be separated through a reverse phase column. As the reverse phase column, columns comprising silica gels having a methyl, ethyl, octyl, or octadecyl group chemically bonded thereto are typically used. The desired moss oil can be separated with a solvent system, containing as a main constituent methanol, by using a UV detector so that the hematommates and atranolins are not contained in the separated moss oil.

EXAMPLES

The present invention now will be further illustrated by, but is by no means limited to, the following Comparative Examples and Examples, wherein all parts and percentages are expressed on a weight basis, unless otherwise specified.

Comparative Example 1

The allergenicity tests of commercially available oakmoss oils, treemoss oils, and cedarmoss oils were carried out. The results are shown in Table 1. As is clear from the results shown in Table 1, natural moss oils have strong allergenicity.

TABLE 1

| Sample | Challenge test concentration (%, acetone) | Mean response |
|---|---|---|
| Oakmoss oil #1 | 1.0% | 3.9 |
| Oakmoss oil #2 | 1.0% | 4.8 |
| Oakmoss oil #3 | 1.0% | 2.0 |
| Oakmoss oil #4 | 1.0% | 2.8 |
| Treemoss oil #1 | 1.0% | 3.0 |
| Treemoss oil #2 | 1.0% | 3.4 |
| Cedarmoss oil #1 | 1.0% | 2.6 |
| Cedarmoss oil #2 | 1.0% | 3.4 |

Induction: 10% acetone solution of oakmoss oil #1

The allergenicity test was carried out as follows.

Ten healthy Hartley strain albino guinea pigs weighing between 380 g and 450 g were used as a group of test animals. The test was carried out according to a Modified Maximization Test (Sato, Y. et al: A modified technique of guinea pig testing to identify delayed hypersensitivity allergens; Contact Dermatitis, 7, 225–237, 1981).

The inducing or sensitizing treatment was first conducted by injecting Freund's Complete Adjuvant (available from Difco Co., Ltd., i.e., "FCA" hereinbelow) intradermally at the shoulder region of the guinea pigs in an amount of 0.1 ml at each of four point. Then a criss-cross lattice of abrasives made at each injection site. A 0.1 ml amount of the sample to be tested was applied to lint cloths (i.e., Torii adhesive tape for a patch test) and the cloths were applied to the injected sites occlusively for 72 hours.

After 7 days from the intradermal injection, the injected sites were shaved and a 10 (W/W)% concentration of sodium lauryl sulfate in white petrolatum was applied to each injected site. After one day, 0.2 ml of test material was applied occlusively for 48 hours. Thus, the inducing treatment was completed.

After 21 days from the intradermal injection, 10 μl of the test sample solutions in acetone having the challenge concentrations listed in Table 1 were applied topically to the shaved back skin of the sensitized guinea pigs (i.e. challenge test) under an open air environment.

As a control, ten guinea pigs, in which only an emulsion obtained by emulsifying FCA with an equal amount of water was intradermally injected during the sensitizing treatment, were used and the challenge test was carried out in the same manner as described above. Thus, the non-specific skin irritation reaction of the test sample was distinguished. The results were examined after 24 and 48 hours from the application. The observation or evaluation was based on the following scoring criteria

| | | Score |
|---|---|---|
| (1) | Formation of Erythema | |
| | no erythema | 0 |
| | slight erythema | 1 |
| | well defined erythema | 2 |
| | moderate to strong erythema | 3 |
| | severe strong erythema to slight eschar formation | 4 |
| (2) | Formation of Edema | |
| | no edema | 0 |
| | slight edema | 1 |
| | moderate edema | 2 |
| | severe edema | 3 |

$$\text{Fractional Response} = \frac{\text{Number of positively reacting animals}}{\text{Number of animals tested}}$$

$$\text{Mean response} = \frac{\Sigma\,(\text{Score of erythema} + \text{Score of edema})}{\text{Number of animals tested}}$$

Comparative Example 2.

Figure 2:
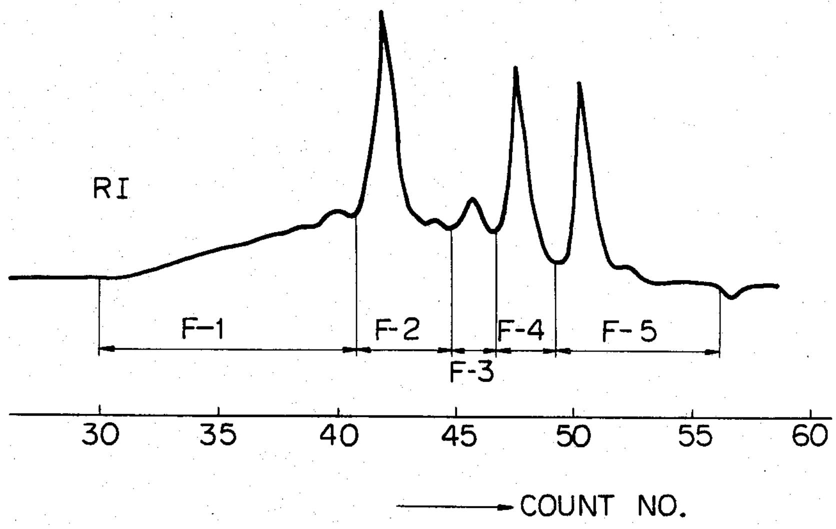
FIG. 2 is a GPC chromatogram of commercially available treemoss oil #1.
Figure 3:
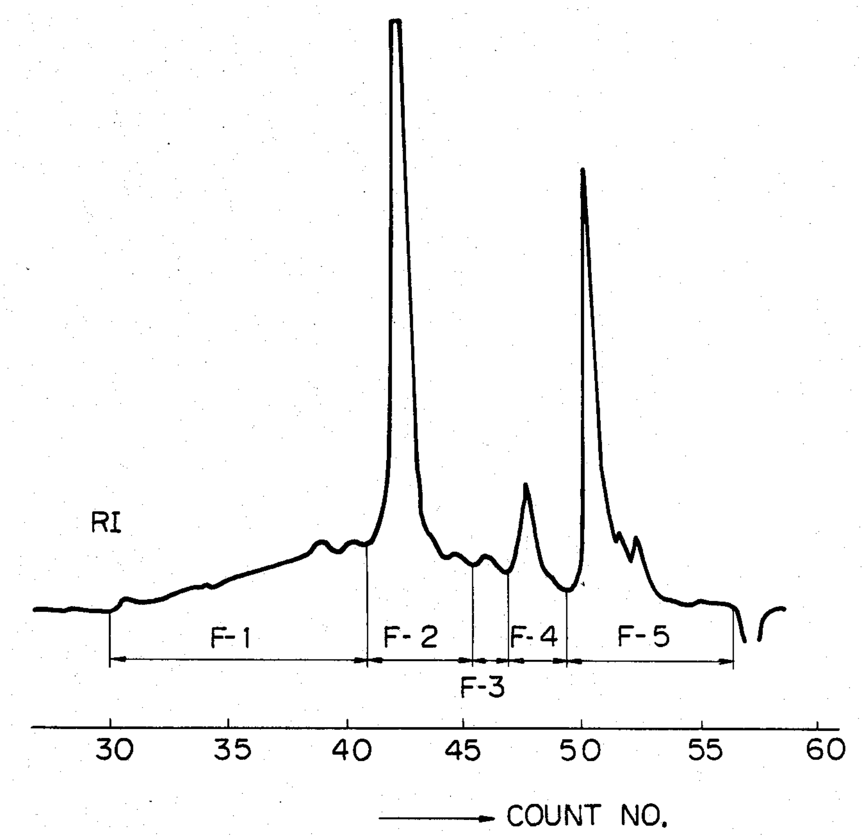
FIG. 3 is a GPC chromatogram of commercially available cedarmoss oil #1.

FIG. 1 illustrates a GPC chromatogram and the fractions separated by preparative GPC of the oakmoss oil #1. FIGS. 2 and 3 illustrate GPC chromatograms of commercially available treemoss oil #1 and cedarmoss oil #1. As shown in FIGS. 1, 2, and 3, and as known in the art, these natural moss oils exhibit similar chromatograms since the components contained therein are similar to each other. On the other hand, it is known in the art that the components contained in moss oils derived from the same type of moss are sometimes largely different from each other depending upon, for example, the origin or the type of extraction solvents.

Figure 4:
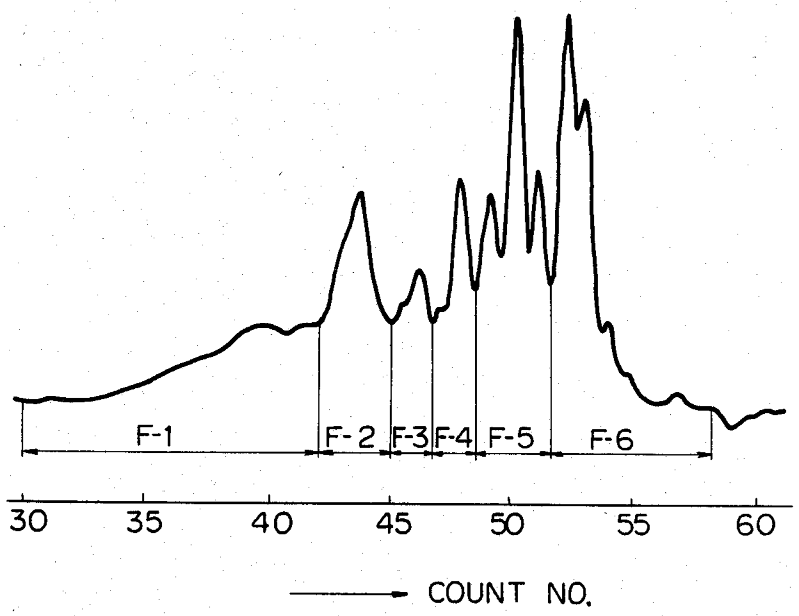
FIG. 4 is a GPC chromatogram and a GPC separation fraction of commercially available oakmoss oil #2.
Figure 5:
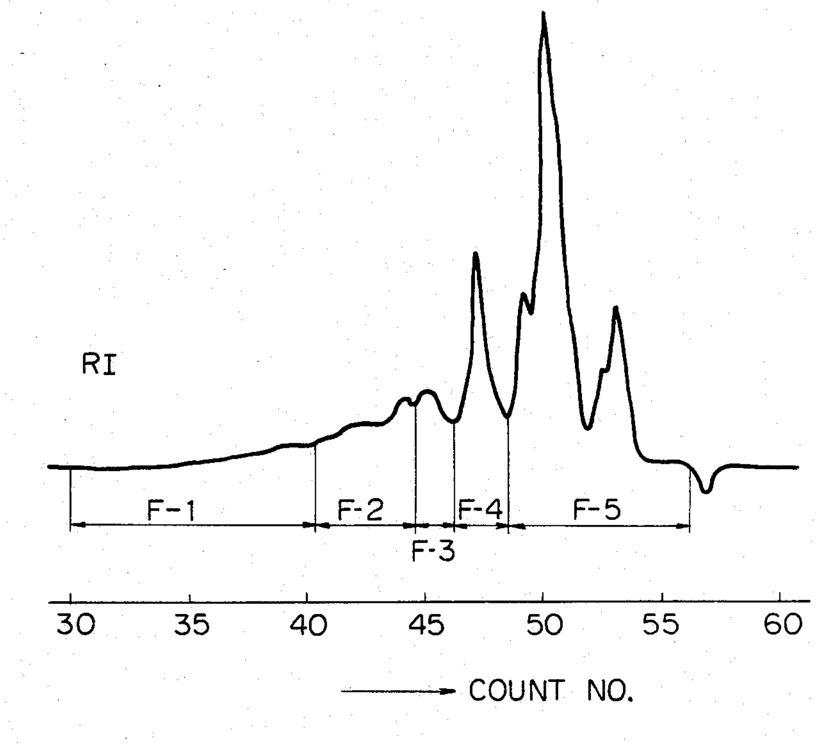
FIG. 5 is a GPC chromatogram of commercially available oakmoss oil #3.
Figure 6:
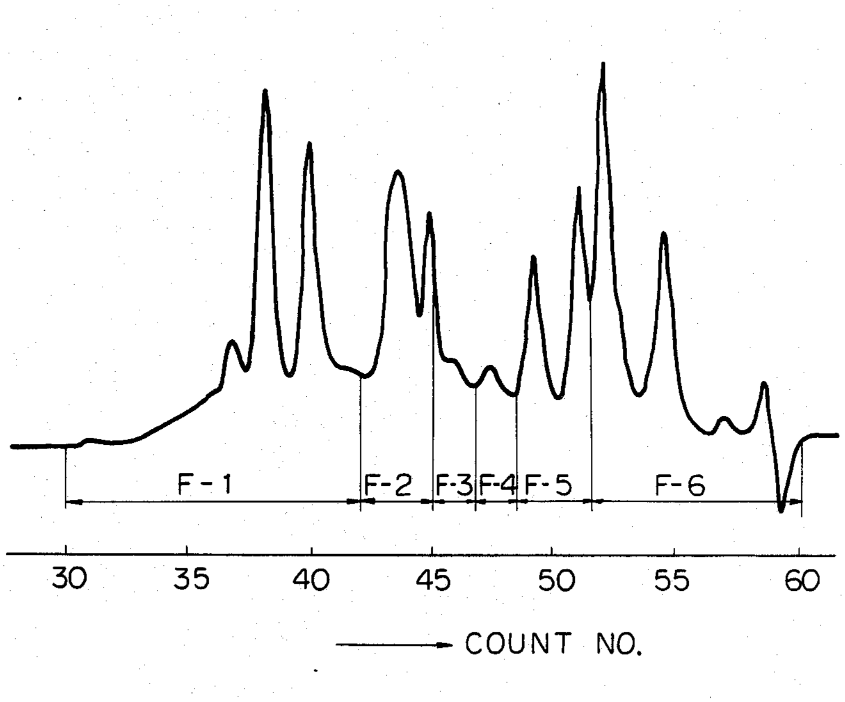
FIG. 6 is a GPC chromatogram of commercially available oakmoss oil #4.

FIGS. 4, 5, and 6 illustrate the GPC chromatograms and the fractions separated by preparatory GPC of the oakmoss oils #2, #3, and #4 in Table 1, respectively. As is clear from the comparison of FIG. 1 with FIGS. 4, 5, and 6, it is not unusual that the GPC chromatograms of commercially available oakmoss oils are different.

The preparative GPC separation conditions were the same as in the above-mentioned case, except that the sample injection concentration was 20%. The allergenicity test results of the oakmoss oil fraction Nos. 1 and 2 obtained as GPC separated fractions, as shown in FIGS. 1 and 4, are shown in Tables 2 and 3.

The concentrations of the challenge test were such that the total amounts were adjusted to 1.0% and that the compositions of the challenge test correspond to those of each fraction. As a result, it became clear which fractions affect the overall allergenicity of the moss oil.

TABLE 2

| Sample | Challenge test concentration (%, acetone) | Mean response |
|---|---|---|
| GPC separated fraction (F-1) | 0.18 | 0.2 |
| GPC separated fraction (F-2) | 0.36 | 1.8 |
| GPC separated fraction (F-3) | 0.10 | 0.0 |
| GPC separated fraction (F-4) | 0.10 | 0.0 |
| GPC separated fraction (F-5) | 0.26 | 1.6 |

Induction: 10% acetone solution of oakmoss oil #1

TABLE 3

| Sample | Challenge test concentration (%, acetone) | Mean response |
|---|---|---|
| GPC separated fraction (F-1) | 0.22 | 0.6 |
| GPC separated | 0.14 | 0.4 |

TABLE 3-continued

| Sample | Challenge test concentration (%, acetone) | Mean response |
|---|---|---|
| fraction (F-2) | | |
| GPC separated fraction (F-3) | 0.14 | 0.0 |
| GPC separated fraction (F-4) | 0.10 | 0.0 |
| GPC separated fraction (F-5) | 0.15 | 1.6 |
| GPC separated fraction (F-6) | 0.25 | 0.6 |

Induction: 10% acetone solution of oakmoss #2

As is clear from the results shown in Tables 2 and 3, the fractions F-2 and F-5 in the case of the oakmoss oil #1 and the fractions F-1, F-2, F-5, and F-6 in the case of the oakmoss oil #2 had a strong allergenicity. A similar tendency was shown in the case of treemoss oil and cedarmoss oil.

Figure 7:
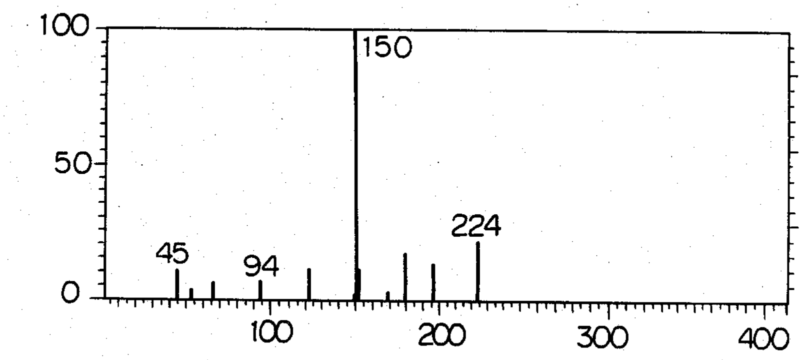
FIG. 7 is mass spectra of ethyl hematommate and ethyl chlorohematommate.
Figure 7:
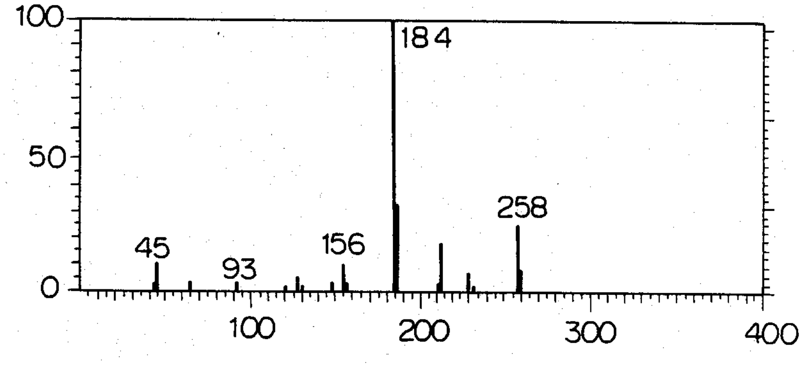

Thus, the substances included in the fraction F-2 in Table 2 were identified as a group A (i.e., substances A) and, furthermore, it was found that ethyl hematommate and ethyl chlorohematommate were contained, as the allergenic components, in the fraction F-5 of Table 2. The mass spectra of these compounds are shown in FIG. 7.

The allergenicity test results of these compounds are shown in Table 4.

TABLE 4

| Sample | Challenge test concentration (%, acetone) | Mean response |
|---|---|---|
| Ethyl hematommate | 0.1 | 1.5 |
| Ethyl chlorohe-matommate | 0.1 | 2.0 |

Induction: 10% acetone solution of oakmoss oil #1

As is clear from the results shown in Table 4, these compounds have a strong allergenicity even in the very low concentration.

Furthermore, the substances included in the fractions F-1 and F-2 in Table 3 were identified as a group B (i.e., substances B). From the analysis of the components contained in the fraction F-5, it has been found that atranorin and chloroatranorin are contained as the main allergenic substances in the fraction F-5.

The allergenicity results of these compounds are shown in Table 5.

TABLE 5

| Sample | Challenge test concentration (%, acetone) | Mean response |
|---|---|---|
| Atranorin | 0.1 | 1.1 |
| Chloroatranorin | 0.1 | 1.3 |

Induction: 10% acetone solution of oakmoss oil #2

As is clear from the results shown in Table 5, atranorin and chloroatranorin have a strong allergenicity even in the very low concentration.

Furthermore, it has been confirmed that the allergenic substances contained in the fraction F-6 of Table 3 were ethyl hematommate and ethyl chlorohematommate.

The above-mentioned results have been also confirmed similarly in the case of commercially available treemoss oil.and cedarmoss oil.

Example 1

Combination of preparative column chromatography and preparative HPLC

A 10 g amount of the oakmoss oil #1 (i.e., absolute oil) used in comparative Example 1 to preparative column chromatography (i.e.,"CC" in the Table hereinbelow). That is, the oakmoss oil was treated with 3 liters of a mixed solvent (i.e., 1 liter of hexane, 1 liter of hexane/ether (90/10), and hexane/ether (80/20)) in a column packed with 200 g silica gel (i.e., Kieselgel 60 available from MERCK & Co., Inc.)

Thus, 4.3 g of the treated oakmoss oil having no substances A shown in FIG. 1 was obtained. The treated oil had a good odor, which was substantially the same as that of the untreated oil.

Figure 8:
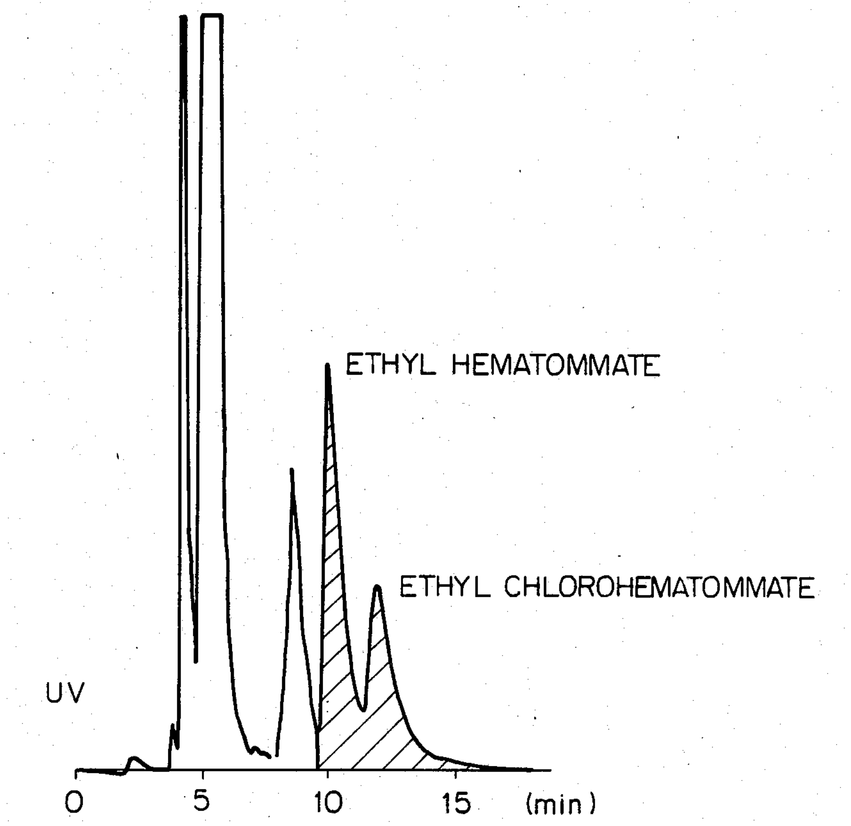
FIG. 8 is an HPLC chromatogram of oakmoss oil #1 obtained by a preparative column chromatography (silica gel) from which the hatched parts were removed.

However, as shown in FIG. 8, the treated oil contained the allergenic substances, ethyl hematommate and ethyl chlorohematommate. Accordingly, the treated oil was then subjected to preparative HPLC under the conditions shown in Table 6 to remove the ethyl hematommate and, thereafter, in the preparative column as shown in FIG. 8. The yield was 3.4 g.

TABLE 6

| | |
|---|---|
| Apparatus: | Nippon Bunko TRIROTAR SR-2 |
| Column: | Finepak SIL C 18 (4.6 mmφ × 250 mm) |
| Solvent: | Methanol-water-acetic acid (80:20:0.1) |
| Flow rate: | 1.0 ml/min. |
| Detecting wavelength: | UV 270 nm |

The allergenicity test of the resultant oakmoss oil was carried out in the same manner as mentioned above, except that the challenge test concentration was changed depending upon the yield (e.g., 0.5% in the case of a yield of 50%).

The allergenicity test result is shown in Table 7.

TABLE 7

| Sample | Challenge test concentration (%, acetone) | Mean response |
|---|---|---|
| CC-HPLC treated Oakmoss oil #1 | 0.34 | 0.0 |

Induction: 10% acetone solution of oakmoss oil #1

As is clear from the result shown in Table 7, the desired oakmoss oil having no allergenicity was obtained by the combination of the preparative column chromatography and the preparative HPLC.

The organoleptic test regarding the odor of the oakmoss oil before and after the CC-HPLC treatment was carried out using a panel composed of 5 specialists. As a result, it was found that the odor of the treated oakmoss oil was as good as that of the untreated oakmoss oil.

Example 2

Combination of preparative column chromatography and preparative HPLC

A 10 g amount of the treemoss oil used in comparative Example 1 was subjected to preparative column chromatography. That is, the treemoss oil was treated with 3 liters of a mixed solvent (i.e., 1 liter of hexane, 1 liter of hexane/ether (90/10), and hexane/ether (80/20)) in a column packed with 200 g of silica gel (i.e., Kieselgel 60 available from MERCK & Co., Inc.)

Thus, 3.9 g of the treated treemoss oil having no substances A shown in FIG. 2 was obtained. The treated oil had a good odor, which was substantially the same as that of the untreated oil.

However, the treated oil contained the allergenic substances, ethyl hematommate and ethyl chlorohematommate. Accordingly, the treated oil was then subjected to preparative HPLC under the conditions shown in Table 6 above to remove the ethyl hematommate and thereafter in the preparative column, similarly as shown in FIG. 8. The yield was 3.6 g. The allergenicity test result of the resultant treemoss oil (i.e., CC-HPLC treated treemoss oil) is shown in Table 8.

TABLE 8

| Sample | Challenge test concentration (%, acetone) | Mean response |
|---|---|---|
| CC-HPLC treated treemoss oil #1 | 0.36 | 0.0 |

Induction: 10% acetone solution of oakmoss oil #1

As is clear from the result shown in Table 8, the desired treemoss oil having no allergenicity was obtained by the combination of the preparative column chromatography and the preparative HPLC.

The organoleptic test regarding the odor of the treemoss oil before and after the CC-HPLC treatment was carried out using a panel composed of 5 specialists. As a result, it was found that the odor of the treated treemoss oil was as good as that of the untreated treemoss oil.

The above-mentioned treatments and allergenicity and organoleptic tests were also carried out with respect to commercially available other oakmoss oils #2, #3, and #4, another treemoss oil #2, and cedarmoss oils #1 and #2. As a result, moss oils having no allergenicity were obtained. There was no substantial difference in the odor of the moss oils before and after treatment.

Example 3

Combination of preparative GPC and preparative HPLC

A 1 g amount of the oakmoss oil in #1 used in Comparative Example 1 was dissolved in THF to form a 20 (W/V)% solution. The fractions F-1 and F-2 (i.e., substances A) were removed from the solution according to the preparative GPC conditions mentioned above. The yield of the treated oakmoss oil was 0.46 g.

Ethyl hematommate and ethyl chlorohematommate were removed from the oakmoss oil obtained above according to the preparative HPLC method shown in Example 1. The yield of the treated oakmoss oil was 0.4 g.

The allergenicity test result of the oakmoss oil (i.e., GPC-HPLC treated oakmoss oil) finally obtained is shown in Table 9.

TABLE 9

| Sample | Challenge test concentration (%, acetone) | Mean response |
|---|---|---|
| GPC-HPLC treated oakmoss oil #1 | 0.4 | 0.0 |

Induction: 10% acetone solution of oakmoss oil #1

As is clear from the result shown in Table 9, the desired oakmoss oil having no allergenicity was obtained by the combination of the preparative GPC and the preparative HPLC.

The organoleptic test regarding the odor of the oakmoss oil before and after the treatment was carried out in the same manner as mentioned above. As a result, it was found that the odor of the treated oil was as good as that of the untreated oil.

Example 4

Hydrogenation treatment

A 10 g amount of oakmoss oil #3 (i.e.,absolute coloress oil) was dissolved in 35 ml of ethanol purified by distillation. The resultant solution was charged to a 100 ml three-necked round-bottom flask and 1 g of a 10% Pd/C catalyst was added thereto. The flask was allowed to stand at room temperature and normal pressure for 24 hours under a hydrogen atmosphere, while stirring with a stirrer. After 24 hours, the reaction mixture was filtered through a cylindrical funnel type glass filter provided with a filter paper, followed by washing, three times, with 90 ml of 99.5% ethanol. The filtrate and the washing filtrate were combined and the ethanol was removed under a reduced pressure. Thus, 8.6 g of the treated (or hydrogenated) oil was obtained.

The allergenicity test result of the hydrogenated oil is shown in Table 10.

TABLE 10

| Sample | Challenge test concentration (%, acetone) | Mean response |
|---|---|---|
| Hydrogenated oakmoss oil #3 | 0.86 | 1.2 |

Induction: 10% acetone solution of oakmoss oil #1

As is clear from the result shown in Table 10, the oakmoss oil having a reduced allergenicity can be obtained only by the hydrogenation treatment.

The organoleptic test regarding the odor of the oakmoss oil before and after the hydrogenation treatment was carried out using a panel composed of 5 specialists. As a result, it was found that the odor of the treated oakmoss oil was as good as that of the untreated oakmoss oil.

The above-mentioned treatments and allergenicity and organoleptic tests were also carried out with respect to commercially available other oakmoss oils, treemoss oils, and cedarmoss oils. As a result, the moss oils having reduced allergenicity were obtained. There was no substantial difference in the odor of the moss oils before and after the treatment.

Example 5.

Alkaline treatment

A 10 g amount of the oakmoss oil #3 used in Example 4 was dissolved in 20 liters of $10^{-3}$N NaOH in ethanol solution and the resultant solution was allowed to stand for 24 hours at a constant temperature bath having a temperature of 5° C. After 24 hours, the solution was neutralized with 0.5N HCl and the solvent was then removed under a reduced pressure. The residue was extracted with acetone, followed by filtration. The acetone was then removed under a reduced pressure to obtain 9.6 g of the alkaline treated (i.e., AL) oil.

The allergenicity test result of the resultant oakmoss oil (i.e., AL-oakmoss oil) is shown in Table 11.

TABLE 11

| Sample | Challenge test concentration (%, acetone) | Mean response |
|---|---|---|
| AL oakmoss oil #3 | 0.96 | 1.7 |

Induction: 10% acetone solution of oakmoss oil #1

As is clear from the result shown in Table 11, the oakmoss oil having reduced allergenicity was obtained by the alkaline treatment.

The organoleptic test regrading the odor of the oakmoss oil before and after the treatment was carried out in the same manner as mentioned above. As a result, it was found that the odor of the treated oil was as good as that of the untreated oil.

Example 6

Combination of preparative column chromatography and hydrogenation treatment

A 10 g amount of the oakmoss oil #1 used in comparative Example 1 was subjected to preparative column chromatography (i.e., "CC" in the Table hereinbelow). That is, the oakmoss oil was treated with 3 liters of mixed solvent (i.e., 1 liter of hexane, 1 liter of hexane/ether (90/10), and hexane/ether (80/20) in a column packed with 200 g of silica gel (i.e., Kieselgel 60 available from MERCK & C., Inc.).

Thus, 4.3 g of the treated oakmoss oil having no substances A shown in FIG. 1 was obtained. The treated oil had a good odor, which was substantially the same as that of the untreated oil. However, as shown in FIG. 8, the treated oil contained the allergenic substances, hematommates.

The analytical conditions are shown in Table 6.

Accordingly, 4.3 g of the treated oil obtained above was dissolved in 20 ml of ethanol purified by distillation and was then hydrogenated by adding 0.4 g of a 10% Pd/C catalyst in the same manner as mentioned in Example 4. The yield of the hydrogenated oil was 3.8 g.

The allergenicity test result of the treated oakmoss oil finally obtained (i.e., CC-hydrogenated oakmoss oil #1 (1)) is shown in Table 12.

TABLE 13

| Sample | Challenge test concentration (%, acetone) | Average score |
|---|---|---|
| CC-hydrogenated oakmoss oil #1 (1) | 0.38 | 0.5 |

Induction: 10% acetone solution of oakmoss oil #1

As is clear from the result shown in Table 12, the oaxmoss oil having a remarkably reduced allergenicity was obtained by the combination of the preparative column chromatography and the hydrogenation treatment.

Figure 9:
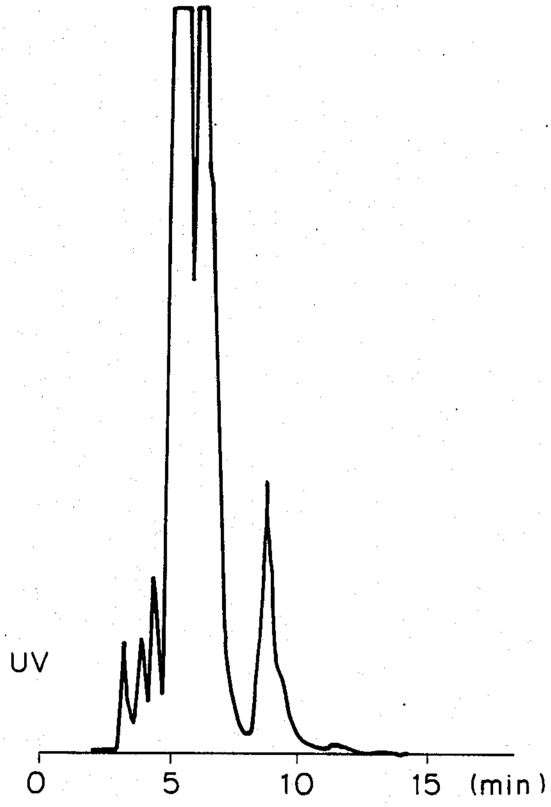
FIG. 9 is an HPLC chromatogram of oakmoss oil #1 obtained by a preparative column chromatography and hydrogenation, treatment.

The HPLC chromatogram of the resultant CC-hydrogenated oakmoss oil is shown in FIG. 9. As is clear from the comparison of FIG. 8 with FIG. 9, the hematommates were converted to other compounds.

The organoleptic test regarding the odor of the oakmoss oil before and after the treatment was carried out in the same manner as mentioned above. As a result, it was found that the odor of the treated oil was as good as that of the untreated oil.

Example 7

Combination of preparative column chromatography and hydrogenation treatment

A 10 g amount of the oakmoss oil #1 used in comparative Example 1 was subjected to preparative column chromatography. That is, the oakmoss oil was treated with 4 liters of a mixed solvent (i.e., 1 liter of hexane, 1 liter of hexane/ether (90/10), hexane/ether (80/20), and hexane/ether (70/30)) in a column packed with 200 g of silica gel (i.e., Kieselgel 60 available from MERCK & Co., Inc.).

Thus, 5.4 g of the treated oakmoss oil having no substances A shown in FIG. 1 was obtained. The treated oil had a good odor, which was substantially the same as that of the untreated oil.

However, the treated oil contained the hematommates similarly as in Example 6. Accordingly, 5.4 g of the treated oil mentioned above was dissolved in 20 ml of ethanol purified by distillation and was then hydrogenated by adding 0.5 g of a Raney nickel catalyst (W6) in the same manner as in Example 4. The yield was 4.7 g.

The allergenicity test result of the treated oakmoss oil (i.e., CC-hydrogenated oakmoss oil #1 (2)) finally obtained is shown in Table 13.

TABLE 13

| Sample | Challenge test concentration (%, acetone) | Mean response |
|---|---|---|
| CC-hydrogenated oakmoss oil #1 (2) | 0.47 | 0.5 |

Induction: 10% acetone solution of oakmoss oil #1

As is clear from the result shown in Table 13, the oakmoss oil having a remarkably reduced allergenicity was obtained by the combination of the preparative column chromatography and the hydrogenation treatment.

The organoleptic test regarding the odor of the oakmoss oil before and after the treatment was carried out in the same manner as mentioned above. As a result, it was found that the odor of the treated oil was as good as that of the untreated oil.

Example 8

Combination of preparative column chromatography and hydrogenation treatment A 10 g amount of the treemoss oil #1 used in Comparative Example 1 was subjected to preparative column chromatography. That is, the treemoss oil was treated with 3 liters of a mixed solvent (i.e., 1 liter of hexane, 1 liter of hexane/ether (90/10), and hexane/ether (80/20)) in a column packed with 200 g of silica gel (i.e., Kieselgel 60 available from MERCK & Co., Inc.)

Thus, 3.5 g of the treated treemoss oil having no substances A shown in FIG. 2 was obtained. The treated oil had a good odor, which was substantially the same as that of the untreated oil.

However, the treated oil contained the hematommates similarly as in Example 6. Accordingly, 3.5 g of the treated oil mentioned above was dissolved in 20 ml of ethanol purified by distillation and was then hydrogenated by adding 0.4 g of a 10% Pd/C catalyst in the same manner as in Example 4. The yield was 3.0 g.

The allergenicity test result of the treated treemoss oil (i.e., CC-hydrogenated treemoss oil) finally obtained is shown in Table 14.

TABLE 14

| Sample | Challenge test concentration (%, acetone) | Mean response |
|---|---|---|
| CC-hydrogenated treemoss oil #1 | 0.30 | 0.3 |

Induction: 10% acetone solution of oakmoss oil #1

As is clear from the result shown in Table 14, the treemoss oil having a remarkably reduced allergenicity was obtained by the combination of the preparative column chromatography and the hydrogenation treatment.

The organoleptic test regarding the odor of the treemoss oil before and after the treatment was carried out in the same manner as mentioned above. As a result, it was found that the odor of the treated oil was as good as that of the untreated oil.

Example 9

Combination of preparative column chromatography, alkaline treatment, and hydrogenation treatment A 10 g amount of the oakmoss oil 19 1 used in comparative Example 1 was subjected to preparative column chromatography. That is, the oakmoss oil was treated with 3 liters of a mixed solvent (i.e., 1 liter of hexane, 1 liter of hexane/ether (90/10), and hexane/ether (80/20)) in a column packed with 200 g of silica gel (i.e., Kieselgel 60 available from MERCK & Co., Inc.).

Thus, 4.4 g of the treated oakmoss oil having no substances A shown in FIG. 1 was obtained. The treated oil had a good odor, which was substantially the same as that of the untreated oil.

A 4.4 g amount of the treated oakmoss oil was then dissolved in 8.8 liters of $10^{-3}$N NaOH in ethanol solution and the resultant solution was allowed to stand for 24 hours at a constant temperature bath having a temperature of 50° C. After 24 hours, the solution was neutralized with 0.5N HCl and the solvent was then removed under a reduced pressure. The residue was extracted with acetone, followed by filtration. The acetone was then removed under a reduced pressure to obtain 3.7 g of the alkaline treated (i.e., AL) oil.

A 3.7 g amount of the treated oil was then dissolved in 20 ml of ethanol purified by distillation and was then hydrogenated by adding 0.3 g of a 10% Pd/C catalyst in the same manner as in Example 4. The yield was 3.4 g.

The allergenicity test result of the treated oakmoss oil (i.e., CC-AL-hydrogenated oakmoss oil #1) finally obtained is shown in Table 15.

TABLE 15

| Sample | Challenge test concentration (%, acetone) | Mean response |
|---|---|---|
| CC-AL-hydrogenated oakmoss oil #1 | 0.34 | 0.3 |

Induction: 10% acetone solution of oakmoss oil #1

As is clear from the result shown in Table 15, the oakmoss oil having a remarkably reduced allergenicity was obtained by the combination of the preparative column chromatography, alkaline treatment, and the hydrogenation treatment.

The organoleptic test regarding the odor of the oakmoss oil before and after the treatment was carried out in the same manner as mentioned above. As a result, it was found that the odor of the treated oil was as good as that of the untreated oil.

Example 10

Combination of preparative column chromatography and preparative HPLC

A 10 g amount of the oakmoss oil ·2 (i.e., concrete oil) was subjected to preparative column chromatography (i.e., "CC" in the Table hereinbelow). That is, the oakmoss oil was treated with 3.3 liters of a mixed solvent (i.e., 0.3 liter of hexane/benzene (50/50), 1 liter of benzene, 1 liter of hexane/ether (90/10), and hexane/ether (80/20)) in a column packed with 200 g of silica gel (i.e., Kieselgel 60 available from MERCK & Co., Inc.).

Thus, 5.7 g of the treated oakmoss oil having no substances B shown in FIG. 4 was obtained. The treated oil had a good odor, which was substantially the same as that of the untreated oil.

Figure 10:
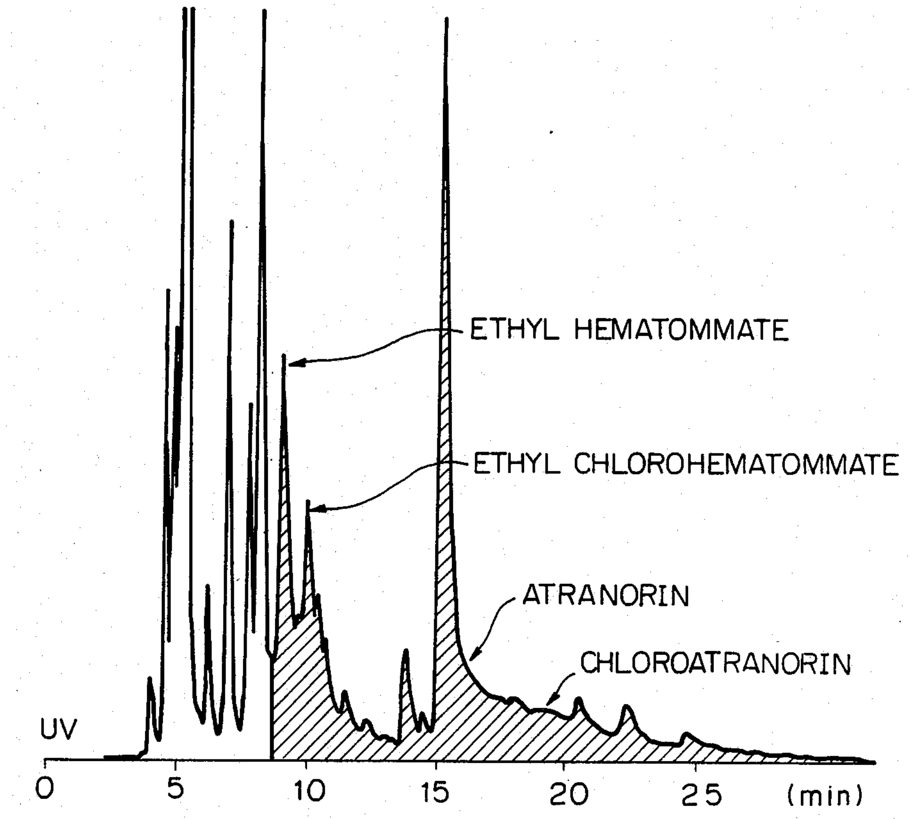
FIG. 10 is an HPLC chromatogram of oakmoss oil #2 obtained by a preparative column chromatography (silica gel) from which the hatched parts were removed.

However, as shown in FIG. 10, the treated oil contained the allergenic substances, hematommates and atranorins. Accordingly, the treat oil was then subjected to preparative HPLC under the conditions shown in Table 16 to remove the ethyl hematommate and thereafter in the preparative column as shown in FIG. 10. The yield was 2.5 g.

TABLE 16

| | |
|---|---|
| Apparatus: | Nippon Bunko TRIROTAR SR-2 |
| Column: | YMS-ODS-A type (7.2 mmφ × 250 mm) |
| Solvent: | Methanol-water-acetic acid (90:10:0.1) |
| Flow rate: | 1.0 ml/min |
| Detecting wavelength: | UV 270 nm |

The allergenicity test result of the resultant oakmoss oil (i.e., CC-HPLC oakmoss oil #2) finally obtained is shown in Table 17.

TABLE 17

| Sample | Challenge test concentration (%, acetone) | Mean response |
|---|---|---|
| CC-HPLC treated oakmoss oil #2 | 0.25 | 1.0 |

Induction: 10% acetone solution of oakmoss oil #2

As is clear from the result shown in Table 17, the oakmoss oil having a reduced allergenicity was obtained by the combination of the preparative column chromatography and the preparative HPLC.

The organoleptic test regarding the odor of the oakmoss oil before and after the CC-HPLC treatment was carried out using a panel composed of 5 specialists. As a result, it was found that the odor of the treated oakmoss oil was as good as that of the untreated oakmoss oil.

Example 11

Combination of preparative column chromatography and preparative HPLC

A 10 g amount of the treemoss oil #2 (i.e., concrete oil) was subjected to preparative column chromatography (i.e., "CC" in the Table hereinbelow). That is, the treemoss oil was treated with 3.3 liters of a mixed solvent (i.e., 0.3 liter of hexane/benzene (50/50), 1 liter of benzene, 1 liter of hexane/ether (90/10), and hexane/ether (80/20)) in a column packed with 200 g of silica gel (i.e., Kieselgel 60 available from MERCK & Co., Inc.).

Thus, 4.4 g of the treated treemoss oil having no substances B shown in FIG. 4 was obtained. The treated oil had a good odor, which was substantially the same as that of the untreated oil.

Figure 11:
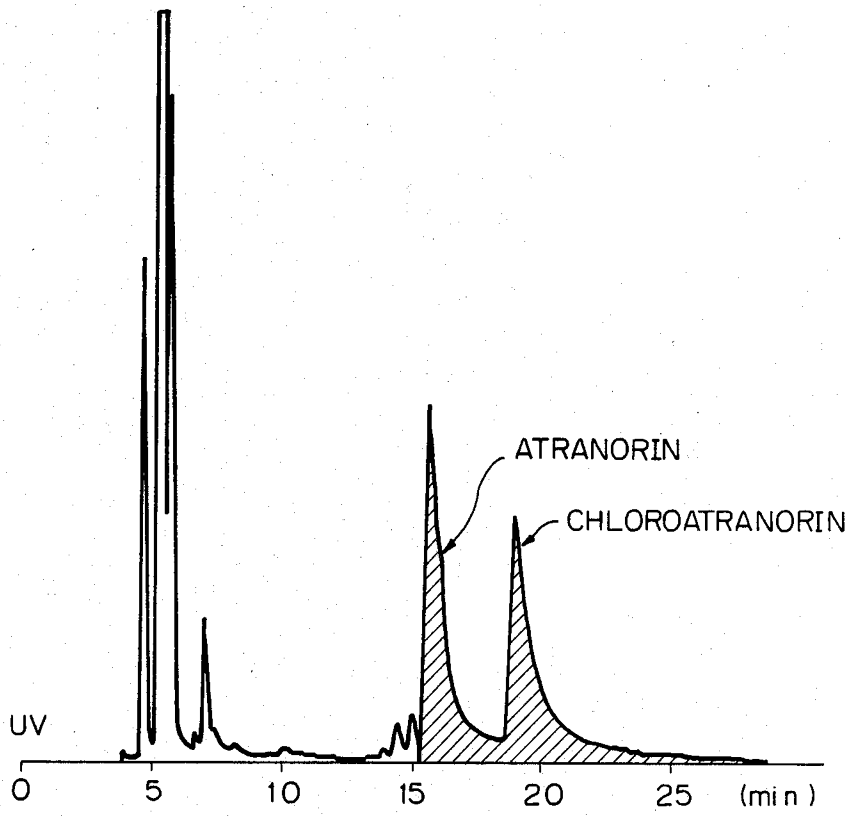
FIG. 11 is an HPLC chromatogram of treemoss oil #2 obtained by a preparative column chromatography in which the hatched parts were removed.

However, the treated oil contained the allergenic substances, atranorin and chloroatranorin. Accordingly, the treated oil was then subjected to preparative HPLC under the conditions shown in Table 16 above to remove the atranorin and thereafter in the preparative column as shown in FIG. 11 the yield was 2.0 g.

The allergenic test result of the treated treemoss oil (i.e., CC-HPLC treated treemoss oil) finally obtained is shown in Table 18.

TABLE 18

| Sample | Challenge test concentration (%, acetone) | Mean response |
|---|---|---|
| CC-HPLC treated treemoss oil #2 | 0.2 | 0.4 |

Induction: 10% acetone solution of oakmoss oil #2

As is clear from the result shown in Table 18, the treemoss oil having a reduced allergenicity was obtained by the combination of the preparative column chromatography and the preparative HPLC.

The organoleptic test regarding the odor of the treemoss oil before and after the CC-HPLC treatment was carried out using a panel composed of 5 specialists. As a result, it was found that the odor of the treated treemoss oil was as good as that of the untreated treemoss oil.

The above-mentioned treatments and allergenicity and organoleptic tests were also carried out with respect to commercially available other oakmoss oils, treemoss oils, and cedarmoss oils. As a result, moss oils having a reduced allergenicity were obtained. There was no substantial difference in the odor of the moss oils before and after the treatment.

Example 12

Combination of preparative column chromatography and hydrogenation treatment

A 10 g amount of the oakmoss oil #2 was subjected to preparative column chromatography (i.e., "CC" in the Table hereinbelow). That is, the oakmoss oil was treated with 3.3 liters of a mixed solvent (i.e., 0.3 liter of hexane/benzene (50/50), 1 liter of benzene, 1 liter of hexane/ether (90/10), and hexane/ether (80/20)) in a column packed with 200 g of silica gel (i.e., Kieselgel 60 available from MERCK & Co., Inc.)

Thus, 5.7 g of the treated oakmoss oil having no substances B shown in FIG. 4 was obtained. The treated oil had a good odor, which was substantially the same as that of the untreated oil.

However, the treated oil contained the allergenic substances, hematommates and atranorins.

Accordingly, 5.7 g of the treated oil obtained above was dissolved in 20 ml of ethanol purified by distillation and was then hydrogenated by adding 0.4 g of a 10% Pd/C catalyst in the same manner as mentioned in Example 4. The yield of the hydrogenated oil was 4.9 g.

The allergenicity test result of the treated oakmoss oil finally obtained (i.e., CC-hydrogenated oakmoss oil #2), is shown in Table 19.

TABLE 19

| Sample | Challenge test concentration (%, acetone) | Mean response |
|---|---|---|
| CC-hydrogenated oakmoss oil #2 | 0.49 | 1.6 |

Induction: 10% acetone solution of oakmoss oil #2

As is clear from the result shown in Table 19, the oakmoss oil having reduced allergenicity was obtained by the combination of the preparative column chromatography and the hydrogenation treatment.

The organoleptic test regarding the odor of the oakmoss oil before and after the treatment was carried out in the same manner as mentioned above. As a result, it was found that the odor of the treated oil was as good as that of the untreated oil.

Example 13

Combination of preparative column chromatography and hydrogenation treatment

A 10 g amount of the oakmoss oil #4 (i.e., resinoid oil) was subjected to preparative chromatography. That is, the oakmoss oil was treated with 3.3 liters of mixed solvent (i.e., 0.3 liter of hexane/benzene (50/50), 1 liter of benzene, 1 liter of hexane/ether (90/10), and hexane/ether (80/20)) in a column packed with 200 g of silica gel (i.e., Kieselgel 60 available from MERCK & Co., Inc.).

Thus, 4.5 g of the treated oakmoss oil having no substances B shown in FIG. 6 was obtained. The treated oil had a good odor, which was substantially the same as that of the untreated oil.

However, the treated oil contained the hematommates and atranorins similarly as in Example 12. Accordingly, 4.5 g of the treated oil mentioned above was dissolved in 15 ml of ethanol purified by distillation and was then hydrogenated by adding 0.5 g of a Raney nickel catalyst (W6) in the same manner as in Example 12. The yield was 4.0 g.

The allergenicity test result of the treated oakmoss oil (i.e., CC-hydrogenated oakmoss oil #4) finally obtained is shown in Table 20.

TABLE 20

| Sample | Challenge test concentration (%, acetone) | Mean response |
|---|---|---|
| CC-hydrogenated oakmoss oil #4 | 0.40 | 0.8 |

Induction: 10% acetone solution of oakmoss oil #2

As is clear from the results shown in Table 20, the oakmoss oil having reduced allergenicity was obtained by the combination of the preparative column chromatography and the hydrogenation treatment.

The organoleptic test regarding the odor of the oakmoss oil before and after the treatment was carried out in the same manner as mentioned above. As a result, it was found that the odor of the treated oil was as good as that of the untreated oil.

Example 14

Combination of preparative column chromatography and hydrogenation treatment

A 100 g amount of oakmoss oil #1 was subjected to preparative column chromatography in a column packed with 1 kg of Sephadex LH-20 (manufactured by Pharmacia Fine Chemicals Co., Ltd.) by using 12 liters of methanol as a solvent. A certain amount of the first fractions was wasted and the remaining 8 liter fraction of the effluent was recovered. The yield was 41 g.

The treated oil obtained above had a good odor, which was substantially the same as that of the untreated oil. However, the resultant treated oil contained the allergenic substances, hematommates.

Accordingly, 41 g of the treated oil was dissolved in 120 ml of ethanol purified by distillation and then hydrogenated by adding 4.0 g of a Raney nickel (W4) catalyst in the same manner as in Example 4. The yield was 38 g.

The allergenicity test of the oakmoss oil finally obtained above (i.e., LH-hydrogenated oakmoss oil #1) was carried out in the same manner as mentioned The allergenicity test result is shown in Table 21.

TABLE 21

| Sample | Challenge test concentration (%, acetone) | Mean response |
|---|---|---|
| LH-hydrogenated oakmoss oil #1 | 0.38 | 0.4 |

Induction: 10% acetone solution of oakmoss oil #1

As is clear from the result shown in Table 21, the oakmoss oil having a reduced allergenicity was obtained by the combination of the preparative column chromatography (i.e., Sephadex) and the hydrogenation treatment.

As a result of HPLC analysis of the LH-hydrogenated oakmoss oil, the hematommates included in the starting oakmoss oil were converted to the other compounds.

The organoleptic test regarding the odor of the oakmoss oil before and after the treatment was carried out in the same manner as mentioned above. As a result, it was found that the odor of the treated oil was as good as that of the untreated oil.

Example 15

Combination of preparative column chromatography and hydrogenation treatment A 100 g amount of cedarmoss oil #1 (i.e., absolute oil) was subjected to preparative column chromatography in a column packed with 1 kg of Sephadex LH-20 (manufactured by Pharmacia Fine Chemicals Co., Ltd.) by using 12 liters of methanol as a solvent. A certain amount of the first fractions was wasted and the remaining 8 liter fraction of the effluent was recovered. The yield was 37 g.

The treated oil obtained above had a good odor, which was substantially the same as that of the untreated oil. However, the resultant treated oil contained the allergenic substances, hematommates.

Accordingly, 37 g of the treated oil was dissolved in 110 ml of ethanol purified by distillation and was then hydrogenated by adding 4.0 g of a Raney nickel (W4) catalyst in the same manner as in Example 4. The yield was 35 g.

The allergenicity test of the cedarmoss oil finally obtained above (i.e., LH-hydrogenated cedarmoss oil #1) was carried out in the same manner as mentioned above The allergenicity test result is shown in Table 22.

TABLE 22

| Sample | Challenge test concentration (%, acetone) | Mean response |
|---|---|---|
| LH-hydrogenated cedarmoss oil #1 | 0.35 | 0.3 |

Induction: 10% acetone solution of oakmoss oil #1

As is clear from the result shown in Table 22, the cedarmoss oil having a reduced allergenicity was obtained by the combination of the preparative column chromatography (i.e., Sephadex) and the hydrogenation treatment.

As a result of HPLC analysis of the LH-hydrogenated cedarmoss oil, the hematommates included in the starting cedarmoss oil were converted to other compounds.

The organoleptic test regarding the odor of the cedarmoss oil before and after the treatment was carried out in the same manner as mentioned above. As a result, it was found that the odor of the treated oil was as good as that of the untreated oil.

Example 16

Combination of preparative column chromatography and alkaline treatment

A 100 g amount of oakmoss oil #1 was subjected to preparative column chromatography in a column packed with 1 kg of Sephadex LH-20 (manufactured by Pharmacia Fine Chemicals Co., Ltd.) by using 10 liters of a mixed solvent of chloroform and methanol (2:1) as a solvent. A certain amount of the first fractions was wasted and the remaining 4 liter fraction of the effluent was recovered. The yield was 49 g.

The treated oil obtained above had a good odor, which was substantially the same as that of the untreated oil. However, the resultant treated oil contained the allergenic substances, hematommates.

Accordingly, 49 g of the treated oil obtained above was dissolved in 5 liters of a $10^{-1}$ N KOH methanol solution (water content =2%) and the resultant solution was allowed to stand for 4 in a constant temperature bath having a temperature of 50° C. After 4 hours, the solution was neutralized with 5 N HCl, followed by removing the solvent under a reduced pressure. Thereafter, the treated oil was extracted with acetone and activated carbon was then added thereto. The acetone extract was filtered and the acetone was removed therefrom under a reduced pressure.

Thus, the alkaline treated (i.e., AL) oakmoss oil was obtained at a yield of 48 g.

The allergenicity test of the oakmoss oil finally obtained above (i.e., LH-AL oakmoss oil #1) was carried out in the same manner as mentioned above. The allergenicity test result is shown in Table 23.

TABLE 23

| Sample | Challenge test concentration (%, acetone) | Mean response |
|---|---|---|
| LH-AL oakmoss oil #1 | 0.48 | 0.4 |

Induction: 10% acetone solution of oakmoss oil #1

As is clear from the result shown in Table 23, the oil having a reduced allergenicity was obtained by the combination of the preparative column chromatography (i.e., Sephadex) and the alkaline treatment.

As a result of HPLC analysis of the LH-AL oakmoss oil, the hematommates included in the starting oakmoss oil were converted to the other compounds.

The organoleptic test regarding the odor of the oakmoss oil before and after the treatment was carried out in the same manner as mentioned above. As a result, it was found that the odor of the treated oil was good, although minor differences were noted when compared with the untreated oil.

Example 17

Combination of preparative column chromatography and alkaline treatment

A 100 g amount of oakmoss oil subjected to preparative column chromatography in a column packed with 1 kg of Sephadex LH-20 (manufactured by Pharmacia Fine Chemicals Co., Ltd.) by using 10 liters of a mixed solvent of chloroform and methanol (2:1) as a solvent. A certain amount of the first fraction was wasted and the remaining 6 liter fraction of the effluent was recovered. The yield was 67 g.

The treated oil obtained above had a good odor, which was substantially the same as that of the untreated oil. However, the resultant treated oil contained the allergenic substances, hematommates and atranorins.

Accordingly, 67 g of the treated oil obtained above was dissolved in 6.7 liters of a $10^{-1}$ N KOH methanol solution (water content =2%) and the resultant solution was allowed to stand for 4hours in a constant temperature bath having a temperature of 50° C. After 4 hours, the solution was neutralized with 5 N HCl, followed by removing the solvent under a reduced pressure. Thereafter, the treated oil was extracted with acetone and activated carbon was then added thereto. The acetone extract was filtered and the acetone was removed therefrom under a reduced pressure.

Thus, the alkaline treated (i.e., AL) oakmoss oil #2 was obtained at a yield of 65 g.

The allergenicity test of the oakmoss oil finally obtained above (i.e., LH-AL oakmoss oil #2) was carried out in the same manner as mentioned above. The allergenicity test result is shown in Table 24.

TABLE 24

| Sample | Challenge test concentration (%, acetone) | Mean response |
|---|---|---|
| LH-AL oakmoss oil #2 | 0.65 | 0.8 |

Induction: 10% acetone solution of oakmoss oil #2

As is clear from the result shown in Table 24, the oakmoss oil having a reduced allergenicity was obtained by the combination of the preparative column chromatography (i.e., Sephadex) and the alkaline treatment.

As a result of HPLC analysis of the LH-AL oakmoss oil, the hematommates and atranorins included in the starting oakmoss oil were converted to other compounds.

The organoleptic test regarding the odor of the oakmoss oil before and after the treatment was carried out in the same manner as mentioned above. As a result, it was found that the odor of the treated oil was good although minor differences were noted when compared with the untreated oil.

Example 18

Combination of preparative column chromatography, hydrogenation and alkaline treatment A 100 g amount of oakmoss oil #1 was subjected to preparative column chromatography in a column packed with 1 kg of Sephadex LH-20 (manufactured by Pharmacia Fine Chemicals Co., Ltd.) by using 10 liters of a mixed solvent of chloroform and methanol (2:1) as a solvent.

Thus, 4 liters of the first fraction (LH-1), 2 liters of the middle fraction (LH-2), and 4 liters of the last fraction (LH-3) were obtained at the yields of 10 g, 41 g, and 49 g, respectively. The fraction LH-3 thus obtained had a good odor, which was substantially the same as that of the untreated oil. However, the fraction LH-3 contained the allergenic substances, hematommates.

Accordingly, 49 g of the fraction LH-3 was dissolved in 120 ml of ethanol purified by distillation and was then hydrogenated by adding 5.0 g of a Raney nickel (W4) catalyst in the same manner as in Example 4. The yield was 46 g.

On the other hand, 41 g of the fraction LH−2, obtained above was dissolved in 4 liters of a $10^{-1}$ N KOH methanol solution (water content=2%) and the resultant solution was allowed to stand for 4 hours in a constant temperature bath having a temperature of 50° C. After 4 hours, the treated LH-2 fraction was neutralized with 5 N HCl, followed by removing the solvent under a reduced pressure. Thereafter, the treated LH-2 fraction was extracted with acetone and activated carbon was then added thereto. The acetone extract was filtered and the acetone was removed therefrom under a reduced pressure. Thus, the alkaline treated (i.e., AL) LH-2 fraction was obtained at a yield of 39 g.

The hydrogenation treated fraction LH-3 and the alkaline treated fraction LH-2 were combined and the allergenicity test of the combined oakmoss oil finally obtained above (i.e., LH-AL-hydrogenated oakmoss oil #1) was carried out in the same manner as mentioned above. The allergenicity test result is shown in Table 25.

TABLE 25

| Sample | Challenge test concentration (%, acetone) | Mean response |
|---|---|---|
| LH-AL-hydrogenated oakmoss oil #1 | 0.85 | 0.8 |

Induction: 10% acetone solution of oakmoss oil #1

As is clear from the result shown in Table 25, the oakmoss oil having a reduced allergenicity was obtained by the combination of the preparative column chromatography (i.e., Sephadex), the hydrogenation and alkaline treatment. Thus, according to this method, a larger amount of the components included in the starting oakmoss oil can be effectively utilized.

As a result of HPLC analysis of the LH-AL-hydrogenated oakmoss oil, the hematommates included in the starting oakmoss oil were converted to other compounds.

The organoleptic test regarding the odor of the oakmoss oil before and after the treatment was carried out in the same manner as mentioned above. As a result, it was found that the odor of the treated oil was good, although minor differences were noted when compared with the untreated oil.

What is claimed is:

1. A hypo-allergenic moss oil from which either one or both of ethyl hematommate and ethyl chlorohematommate are substantially removed.

2. A hypo-allergenic moss oil from which either one or both of atranorin and chloroatranorin are substantially removed.

3. A hypo-allergenic moss oil in which (A) substances having a count number of 40.5 to 45 or (B) substances having a count number of 30 to 45, determined by gel permeation chromatography in four TSKGEL G2000H8 columns under the conditions defined below are substantially removed.

Column temperature: 40° C.,

Solvent: Tetrahydrofuran,

Flow rate: 1.2 ml/min at 90 kg/cm$^2$,

Sample concentration: 0.2 to 2% by weight in tetrahydrofuran,

Sample amount: 100 $\mu$l, and

Detector: Differential refractive index detector.

4. A process for producing hypo-allergenic moss oil in which the hypo-allergenic moss oil is separated from a starting moss oil with at least one treatment selected from the group consisting of chromatography, solvent extraction, countercurrent partition, and membrane separation.

5. A process as claimed in claim 4, wherein the separated hypo-allergenic moss oil is further treated, with either one or both of a catalytic hydrogenation treatment and alkaline treatment.

6. A process for producing hypo-allergenic moss oil in which the hypo-allergenic moss oil is treated with either one or both of a catalytic hydrogenation treatment and alkaline treatment.

* * * * *

UNITED STATES PATENT AND TRADEMARK OFFICE
CERTIFICATE OF CORRECTION

PATENT NO. : 4,663,080

DATED : May 5, 1987

INVENTOR(S) : Yushi Terajima, et al.

It is certified that error appears in the above-identified patent and that said Letters Patent is hereby corrected as shown below:

| | |
|---|---|
| Col. 1, line 24 | After "are" insert --also-- |
| Col. 2, line 50 | After "hydrogenation" delete "," |
| Col. 8, line 7 | After "Example 1" insert --was subjected-- |
| Col. 8, line 62 | After "oil" insert --# 1-- |
| Col. 10, line 54 | After "Example 5" delete "." |
| Col. 10, line 61 | Delete "5°C." and substitute --50°C.-- |
| Col. 11, line 55 | Delete "oaxmoss" and substitute --oakmoss-- |
| Col. 13, line 27 | After "oil" delete "19" and substitute --# 1-- |
| Col. 14, line 11 | Delete ".2" and substitute --#2-- |
| Col. 16, line 24 | After "preparative" insert --column-- |
| Col. 17, line 67 | After "above" insert --.-- |
| Col. 18, line 43 | After "4" insert --hours-- |

UNITED STATES PATENT AND TRADEMARK OFFICE
CERTIFICATE OF CORRECTION

PATENT NO. : 4,663,080

DATED : May 5, 1987

INVENTOR(S) : Yushi Terajima, et al.

It is certified that error appears in the above-identified patent and that said Letters Patent is hereby corrected as shown below:

| | |
|---|---|
| Col. 18, line 65 | Before "oil" insert --oakmoss-- |
| Col. 19, line 15 | After "oil" insert -- # 2 was-- |
| Col. 19, line 32 | Insert space between "4" and "hours" |

Signed and Sealed this

First Day of March, 1988

*Attest:*

DONALD J. QUIGG

*Attesting Officer* *Commissioner of Patents and Trademarks*